United States Patent [19]

van der Stelt et al.

[11] 4,152,441
[45] May 1, 1979

[54] ANALGESIC IMIDAZOLEMETHANOLS

[75] Inventors: Cornelis van der Stelt; Petrus S. Hofman, both of Haarlem, Netherlands

[73] Assignee: Gist-Brocades N.V., Delft, Netherlands

[21] Appl. No.: 329,210

[22] Filed: Feb. 2, 1973

[30] Foreign Application Priority Data

Feb. 4, 1972 [GB] United Kingdom ............... 5418/72
Sep. 5, 1972 [GB] United Kingdom ............. 41182/72

[51] Int. Cl.² .................. A61K 31/415; C07D 233/04
[52] U.S. Cl. ............................... 424/273 R; 548/341; 548/342; 548/343
[58] Field of Search ................. 260/309; 548/342; 424/273 R

[56] References Cited

PUBLICATIONS

Behringer et al., Chem. Ber. 1966, vol. 99, pp. 1815–1821.
Rohr et al., Chem. Ber. 1968, vol. 101, pp. 3491–3498.
Shirley et al., J. Amer. Chem. Soc., 1957, vol. 79, pp. 4922–4927.
Tertov et al., Chem. Abst., 1971, vol. 74, No. 76466e.

*Primary Examiner*—Natalie Trousof
*Assistant Examiner*—Richard A. Schwartz
*Attorney, Agent, or Firm*—Robert E. Burns; Emmanuel J. Lobato; Bruce L. Adams

[57] ABSTRACT

α,α-Diarylimidazole-2-methanols of the general formula

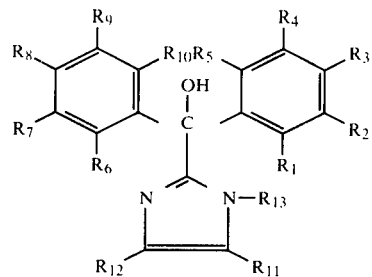

wherein $R_1$–$R_{10}$ are the same or different and each represents a hydrogen or halogen atom or a trifluoromethyl or tertiary butyl group, with at least one of said $R_1$–$R_{10}$ being halogen, trifluoromethyl or tertiary butyl; $R_{11}$ and $R_{12}$ are the same or different and each represents a hydrogen atom, an alkyl group, a phenyl group or a halogen-or trifluoromethyl-substituted phenyl group; and $R_{13}$ represents a hydrogen atom or a lower alkyl group, a lower alkoxymethyl group, a phenylalkyl group (optionally substituted in the phenyl moiety by one or more halogen atoms or alkyl or trifluoromethyl groups), an alkenyl group, a phenyl(lower)alkoxymethyl group (optionally substituted in the phenyl moiety by one or more halogen atoms or alkyl or trifluoromethyl groups) or a benzenesulfonyl group (in which the phenyl moiety is optionally substituted by one or more alkyl groups) are described. These compounds and their non-toxic acid addition salts have anorexient activity. Certain of these compounds have analgesic activity comparable to morphine but without its serious side effects. Processes for their manufacture and compositions for their use are described.

8 Claims, No Drawings

ANALGESIC IMIDAZOLEMETHANOLS

THIS INVENTION relates to new, therapeutically useful α,α-diarylimidazole-2-methanols and acid addition salts thereof, to processes for their preparation and pharmaceutical compositions containing them.

The new α,α-diarylimidazole-2-methanols of the present invention are those of the general formula:

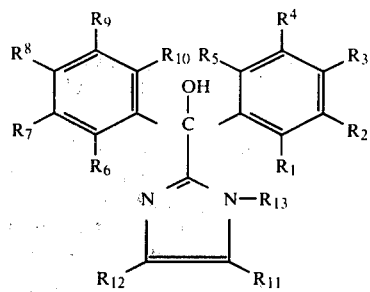

wherein $R_1$–$R_{10}$ are the same or different and each represents a hydrogen or halogen atom or a trifluoromethyl or tertiary butyl group, provided at least one of them is halogen, trifluoromethyl or tertiary butyl, $R_{11}$ and $R_{12}$ are the same or different and each represents a hydrogen atom, a lower alkyl group, a phenyl group or a halogen- or trifluoromethyl-substituted phenyl group and $R_{13}$ represents a hydrogen atom or a lower alkyl group, a lower alkoxymethyl group, a phenylalkyl group (optionally substituted in the phenyl moiety by one or more halogen atoms or alkyl or trifluoromethyl groups), an alkenyl group, a phenyl(lower)alkoxymethyl group (optionally substituted in the phenyl moiety by one or more halogen atoms or alkyl or trifluoromethyl groups) or a benzenesulphonyl group (in which the phenyl moiety is optionally substituted by one or more alkyl groups). The term "lower" used with respect to alkyl and alkoxy groups indicates that the group contains at most 6 carbon atoms.

The α,α-diarylimidazole-2-methanols of general formula I have valuable therapeutic properties. They show anorexiant activity. Within the group of compounds defined by formula I, those in which $R_{13}$ represents a hydrogen atom or, when $R_{11}$ and $R_{12}$ are hydrogen atoms or one or both of them is an alkyl group, a lower alkoxymethyl group or a phenyl(lower)alkoxymethyl group in which the phenyl moiety is optionally substituted by one or more halogen atoms or alkyl or trifluoromethyl groups, have analgesic activity which makes the compounds useful in the relief of pain in humans and animals. They also possess antiphlogistic and antipyretic activity.

As anorexiants the compounds of formula I in which $R_{13}$ is different from hydrogen and, when $R_{11}$ and $R_{12}$ are hydrogen atoms or one or both of them is an alkyl group, from alkoxymethyl or phenyl(lower)alkoxymethyl or substituted phenyl(lower)alkoxymethyl, are preferred.

The most active compounds are those in which $R_3$ and $R_8$ both are a chlorine atom, $R_{11}$ and $R_{12}$ are hydrogen atoms or one of them is a p-chlorophenyl group and $R_1$, $R_2$, $R_4$, $R_5$, $R_6$, $R_7$, $R_9$ and $R_{10}$ are hydrogen atoms. Specifically preferred compounds are α,α-bis(p-chlorophenyl)-1-vinylimidazole-2-methanol and 1-benzyl-α,α-bis(p-chlorophenyl)imidazole-2-methanol and their salts.

Within the above defined group of analgesically active compounds, preferred compounds are those in which $R_3$ is a halogen atom or a trifluoromethyl or tertiary butyl group, $R_8$ is a hydrogen or halogen atom or a trifluoromethyl or tertiary butyl group and $R_1$, $R_2$, $R_4$, $R_5$, $R_6$, $R_7$, $R_9$, $R_{10}$, $R_{11}$ and $R_{12}$ are hydrogen atoms. Specifically preferred are the compounds in which both $R_3$ and $R_8$ are a chlorine atom or $R_3$ is a trifluoromethyl group and $R_8$ is a hydrogen atom. The most active and therefore most preferred compounds are α,α-bis(p-chlorophenyl)imidazole-2-methanol, α,α-bis(p-chlorophenyl)-1-methoxymethylimidazole-2-methanol, α-phenyl-α-(p-trifluoromethylphenyl)imidazole-2-methanol and 1-(methoxymethyl)-α-phenyl-α-(p-trifluoromethylphenyl)imidazole-2-methanol.

Analgesics are usually divided into two main groups according to the type of activity exhibited. After their best known representatives these groups are usually referred to as (a) the morphine-type analgesics and (b) the aspirin-type analgesics. Analgesics of the first type exhibit the stronger activity but are known to have important sometimes serious, disadvantages due to side effects such as sedation, depression of respiration, addiction, physical dependence and intestinal disorders. Analgesics of the second type are also known to cause side reactions which due to the wide variety of structures of compounds commonly classified within this group may vary from gastric lesions for the salicyclic acid derivatives to agranulocytosis for aminopyrine.

The analgesic activity of the compounds of formula I has clearly been established from the results obtained in one or more of the following tests:

(a) Test according to Carrol and Lim, using rats (M. V. Carrol and R. K. S. Lim, Archiv. int. Pharmacodyn 125, 383 (1960));

(b) Test according to Randall and Selitto, using rats (L. O. Randall and J. J. Selitto, Archiv. int. Pharmacodyn. 111, 409–419 (1957));

(c) Test according to d'Amour-Smith (tailflick), using rats (F. E. d'Amour and D. I. Smith, J. Pharm. Exp. Therap. 72, 74–79 (1941));

(d) Hot-plate test, using mice (G. Woolfe and A. D. Macdonald, J. Pharmacol. Exptl. Ther. 80, 300–307 (1944)).

Test (a) enables a certain differentiation to be made between analgesics of the morphine vis-a-vis the aspirin type; in Test (b) analgesics of both types show activity;

Test (c) gives positive results for the very strong analgesics, like morphine;

Test (d) is not very specific. In all the above mentioned tests the compounds indicated above as preferred analgesics show strong activity both upon oral and parenteral application.

The following results were obtained with α,α-bis(p-chlorophenyl)imidazole-2-methanol (hereinafter referred to as "Compound A").

The dose $AD_{100}$ (i.e. the dose which raises the pain threshold by 100%) of Compound A in the Randall Selitto test is 3.4 mg./kg. animal body weight when administered orally (p.o.); the $ED_{50}$ dose (i.e. the dose which protects 50% of the rats) of Compound A in the d'Amour-Smith test is 21 mg./kg. animal body weight (p.o.): for morphine it is 45 mg./kg. p.o.

(e) A special test has been performed with α,α-bis-(p-chlorophenyl)imidazole-2-methanol in order to determine whether the compound might exhibit physical dependence:

Test according to Saelens et al. (J. K. Saelens et al., Arch. int. Pharmacodyn 190 (2), 213–218 (1971) affording a quick check for potential physical dependence as is found for morphine. When Compound A was compared with a number of analgesics belonging to the morphine type, the results were positive for these analgesics and negative for Compound A.

The following observation tests have been performed in order to establish whether the compound causes certain side effects inherent with the administration of morphine:

(f) Observation of the behaviour of dogs upon administration of an analgesic. It is known that morphine causes dogs to vomit and also causes a depression of respiration. Neither of these reactions was caused by Compound A. However, a slight stimulation and antagonism of narcosis and narcosis-induced respiration depression was observed after administration of the compound.

(g) Observation of the behaviour of cats upon administration of an analgesic. Morphine causes such excitement in cats that they are completely uncontrollable; no excitement at all was caused by administration of Compound A.

(h) Observation of the behaviour of rats upon administration of an analgesic. Morphine sedates rats but activation is noted upon administration of Compound A.

The analgesic potency of the most active $\alpha,\alpha$-diarylimidazole 2-methanols of the present invention is comparable with that of morphine; as the compounds do not exhibit the serious side effects of morphine they should not be called "morphine-like". Probably they are to be classified in a third class.

For use as therapeutics the compounds of general formula I may be used as such or as non-toxic acid addition salts, i.e. salts which are not harmful to the animal organism when used in therapeutic doses. Such acid addition salts may be derived from inorganic acids, such as the hydrohalic acids (e.g. hydrochloric and hydrobromic acid) and sulphuric acid, and organic acids such as oxalic, maleic, tartaric, citric, acetic, lactic, succinic, fumaric and pamoic acids.

The dosage and method of administration will depend on the mammalian species and the condition treated. For use as anorexiants in adult humans the oral dosage will be from 25 to 200 mg per person daily. The compounds with analgesic activity are suitably administered orally to humans in daily doses ranging from 5 to 100 mg per person. Injectable solutions for analgetic purposes will generally have a concentration ranging from 0.05 to 2 mg/ml.

According to a feature of the invention, the $\alpha,\alpha$-diarylimidazole-2-methanols of general formula I are prepared by reacting a compound of the general formula:

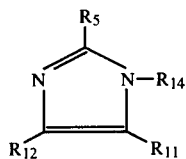

(wherein $R_{15}$ represents an alkali metal (preferably lithium) atom or a reactive organo-metal group, such as a group —MgX, in which X represents a halogen (preferably chlorine or bromine) atom, $R_{14}$ is identical to $R_{13}$ except a hydrogen atom, or a group beyond the scope of $R_{13}$ that is easily removable by, for example, hydrolysis, oxidation or hydrogenation, and $R_{11}$ and $R_{12}$ are as hereinbefore defined) with a compound of the general formula:

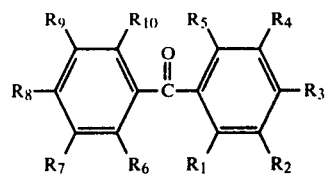

(wherein $R_1$–$R_{10}$ are as hereinbefore defined), and removing the group or atom $R_{15}$ from the resulting organo-metal complex by hydrolysis to yield a desired tertiary alcohol of general formula I wherein $R_{13}$ represents a hydrogen atom or a corresponding compound carrying a substituent group $R_{14}$ on a nitrogen atom of the imidazole nucleus and, when in the latter case the substituent group is not identical to $R_{13}$ in the desired product, removing by methods known per se said substituent group and, if desired, introducing a group within the definition of $R_{13}$ by a method known per se.

The reaction between the compounds of formula II and III is preferably carried out in an inert anhydrous organic solvent (e.g. tetrahydrofuran) or solvent mixture (e.g. tetrahydrofuran and diethyl ether). When $R_{15}$ represents an alkali metal atom it is preferred to perform the reaction at temperatures below 0° C.; when $R_{15}$ represents a group —MgX a solution of the reactants is preferably refluxed.

It should be understood that the definition of $R_{14}$ includes removable groups encompassed by the definition of $R_{13}$ and that when $R_{14}$ is such a group, the compound obtained from the reaction of compounds of formula II and III may be both an intermediate and an end product.

Examples of easily removable groups represented by $R_{14}$ in compounds of the general formula II are toluene-p-sulphonyl, benzyloxymethyl and alkoxyalkyl groups, the methoxymethyl group being preferred. Such groups can all be removed by hydrolysis, thereby affording compounds of general formula I wherein $R_{13}$ represents a hydrogen atom.

The hydrolytic removal of the group $R_{14}$ may take place spontaneously when the product resulting from the reaction between compounds of the general formulae II and III is hydrolysed. Active removal of a group $R_{14}$ by hydrolysis may be effected by heating an aqueous solution of a resulting tertiary alcohol of the general formula:

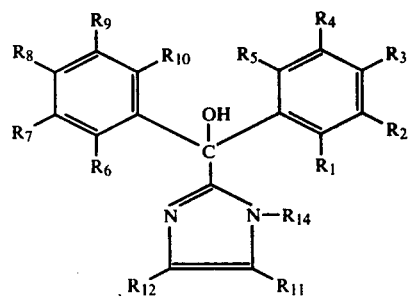

(wherein the various symbols are as hereinbefore defined) to which some acid or base has been added.

When $R_{14}$ is a group removable by oxidation, e.g. allyl, vinyl or prop-1-enyl, the group may be removed from the resulting tertiary alcohol by oxidation with a permanganate, e.g. potassium permanganate, to which some aqueous alkali hydroxide solution has been added. Removal of the allyl group by oxidation is only possible when the double bond is previously shifted to the α-position (i.e. the allyl group becomes prop-1-enyl). In some cases the shifting occurs concurrently with the introduction of the substituent $R_{15}$ in the appropriate imidazole compound to obtain a compound of formula II, especially in those instances where $R_{15}$ represents a lithium atom. Otherwise the shifting is to be brought about by previous treatment with a strong base, e.g. potassium tertiary butoxide in an organic solvent, e.g. dimethyl sulphoxide.

When $R_{14}$ represents a benzyl group, removal thereof can be effected by hydrogenation. The agents suitable for the hydrogenation (e.g. sodium with liquid) ammonia) may interfere with any halogen substituents on the phenyl nuclei. Generally speaking such halogen atoms are more tightly bound the smaller their atomic number and consequently use of the benzyl group as a protective group is only recommended when the symbols $R_1$-$R_{10}$, when other than hydrogen represent a fluorine atom or a trifluoromethyl or tert.-butyl group.

The introduction of a group $R_{13}$ in a compound of formula I in which $R_{13}$ is a hydrogen atom is preferably carried out by reacting the compound of formula I with an appropriate alkyl, alkoxymethyl, substituted or unsubstituted phenylalkyl, alkenyl, substituted or unsubstituted phenylalkoxymethyl or substituted or unsubstituted benzenesulfonyl halide, such as a chloride or bromide. The reaction is preferably carried out in an organic solvent in the presence of a base (e.g. sodium hydroxyde) and a catalytic amount of sodium iodide or potassium iodide.

Compounds of the general formula II wherein $R_{15}$ represents a lithium atom may be prepared by reacting under a nitrogen atmosphere a lithium donating compound, for example butyllithium, with a compound of the general formula:

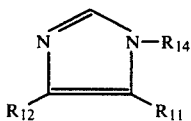

wherein $R_{11}$, $R_{12}$ and $R_{14}$ are as hereinbefore defined. The reaction is preferably carried out in an inert anhydrous organic solvent (e.g. tetrahydrofuran) or solvent mixture (e.g. a mixture of tetrahydrofuran and diethyl ether). Such compounds of the general formula II may be prepared in situ from compounds of the general formula V; they are immediately caused to react upon a compound of the general formula III without previous isolation or purification.

The choice of groups $R_{14}$ is restricted to those groups as are incapable of reacting with atoms or groups represented by $R_{15}$. When $R_{11}$ or $R_{12}$ is a substituted or unsubstituted phenyl group, the compound of formula I in which $R_{13}$ is a hydrogen atom is easily decomposed by hydrolysis. The use of a protecting group $R_{14}$ that is to be removed by hydrolysis should therefore be avoided in those cases.

According to another feature of the invention, the compounds of the general formula I are prepared by reacting a compound of the general formula:

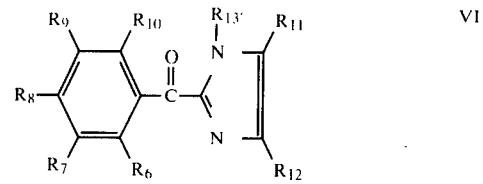

(wherein $R_{13}'$ is a hydrogen atom or a group within the definition of $R_{13}$ or $R_{14}$ and the other R-symbols are as hereinbefore defined) with a compound of the general formula

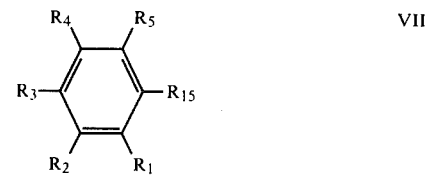

(wherein the R-symbols are as hereinbefore defined), preferably under reaction conditions similar to those hereinbefore described with respect to the reaction between compounds of formulae II and III, removing the atom or group $R_{15}$ from the resulting organo-metal complex by hydrolysis and, if desired, replacing $R_{13}'$ by a substituent within the definition of $R_{13}$ as described above.

The starting materials of formula VI may be prepared by reacting a compound of the general formula:

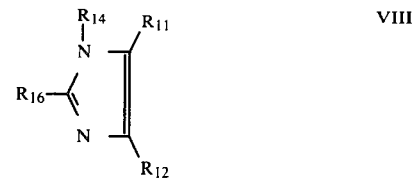

wherein $R_{16}$ represents an alkali metal (preferably lithium) atom or a group —MgX (wherein X represents a halogen, preferably chlorine or bromine, atom) and $R_{11}$, $R_{12}$ and $R_{14}$ are as hereinbefore defined, with a nitrile of the general formula:

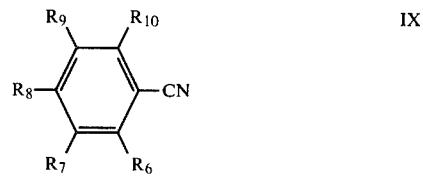

(wherein $R_6$-$R_{10}$ are as hereinbefore defined) and, if desired, removing the group $R_{14}$ and introducing a group $R_{13}'$ by methods hereinbefore described. Preferred reaction conditions are those described for the reaction between compounds of formulae II and III when $R_{15}$ in formula II represents an alkali metal atom or a group —MgX.

According to another feature of the invention, the α,α-bis-arylimidazole-2-methanols of general formula I that are symmetrically substituted in the phenyl groups, i.e. the compounds of the general formula:

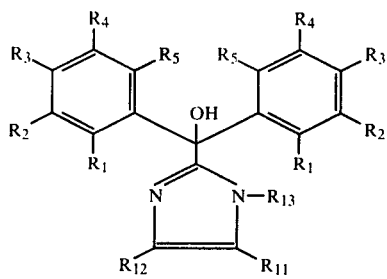

(wherein the various R-symbols are as hereinbefore defined, at least one of $R_1$, $R_2$, $R_3$, $R_4$ and $R_5$ being halogen, trifluoromethyl or tertiary butyl), are prepared by reacting a compound of the general formula:

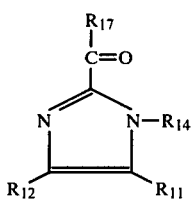
XI (wherein $R_{17}$ represents a halogen atom, an alkoxy, aryloxy, aralkoxy or silyloxy, e.g. trimethylsiloxy, group or a group OM in which M is a metal atom, and $R_{11}$, $R_{12}$ and $R_{14}$ are as hereinbefore defined), with a compound of general formula VII, hydrolysing the resulting organo-metal complex to yield a desired tertiary alcohol of general formula X in which $R_{13}$ represents a hydrogen atom or a corresponding compound carrying a substituent group $R_{14}$ on a nitrogen atom of the imidazole nucleus and, when in the latter case the substituent group is not identical to the group $R_{13}$ in the desired product, removing by methods known per se said substituent group and, if desired, introducing a group within the definition of $R_{13}$ by a method known per se. The reaction is preferably carried out by heating the compound of formula XI with a two-fold molar quantity of the compound of formula VII in an inert anhydrous organic solvent (e.g. tetrahydrofuran and diethyl ether). The group $R_{14}$ may be removed as hereinbefore described.

Compounds of general formula XI may be prepared by reacting an imidazole derivative of the formula II, wherein $R_{15}$ represents a lithium atom, i.e. a compound of the general formula:

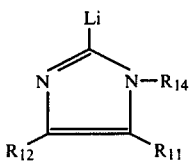
XII (wherein $R_{11}$, $R_{12}$ and $R_{14}$ are as hereinbefore defined) with carbon dioxide to form a lithium salt of an imidazole-2-carboxylic acid of the general formula:

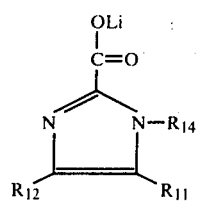
XIII (wherein $R_{11}$, $R_{12}$ and $R_{14}$ are as hereinbefore defined) and, if desired, converting the latter into another compound of formula XI in manner known per se. For example the compound of formula XIII may be reacted with an alkyl halide, aryl halide or aralkyl halide to obtain an alkyl, aryl or aralkyl ester ($R_{17}$=alkoxy, aryloxy or aralkoxy), with a halogenosilane to obtain a silyl ester ($R_{17}$=silyloxy) or with a thionyl halide to obtain an acid halide ($R_{17}$=halogen).

It will be understood that, when $R_{14}$ represents an allyl group, the double bond may be shifted to the α-position concurrently with the preparation of the compound of formula XII as described above for compounds of formula II.

When $R_{17}$ represents an alkoxy, aryloxy or aralkoxy group, the compound of formula XI may also be prepared by reacting a compound of formula V with a halogenoformate of the general formula:

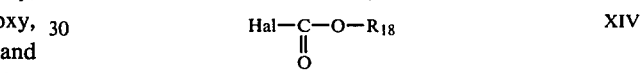
XIV wherein Hal represents a halogen atom and $R_{18}$ represents an alkyl, aryl or aralkyl group. The reaction is preferably carried out by heating the reactants in a polar solvent, such as dimethylformamide or acetonitrile, in the presence of a strong base, e.g. triethylamine.

According to another feature of the invention the compounds of formula I in which $R_{13}$ is a lower alkyl group, a lower alkoxymethyl group, a phenylalkyl group (optionally substituted in the phenyl moiety by one or more halogen atoms or alkyl or trifluoromethyl groups) an alkenyl group, a phenyl(lower)alkoxymethyl group (optionally substituted in the phenyl moiety by one or more halogen atoms or alkyl or trifluoromethyl groups) or a benzenesulphonyl group (in which the phenyl moiety is optionally substituted by one or more alkyl groups), are prepared by introducing by a method known per se the substituent $R_{13}$ in the corresponding compound in which $R_{13}$ is a hydrogen atom. A suitable method is the reaction with an appropriate halide as hereinbefore described.

The following Examples illustrate the preparation of compounds of the present invention.

EXAMPLE I

A. Preparation of α-(p-bromophenyl)-α-phenyl-1-(toluene-p-sulphonyl)imidazole-2-methanol.

To a solution of 33.3 g. (0.15 mol) of 1-(toluene-p-sulphonyl)imidazole (H. A. Staab and K. Wendel, Ber. 93, (1960) 2902) in 300 ml. of anhydrous tetrahydrofuran and 150 ml. of anhydrous diethyl ether at a temperature of −40° to −50° C. under a nitrogen atmosphere were added drop-wise 91 ml. of a 20% solution of butyllithium in n-hexane (0.20 mol.) dissolved in 150 ml. of anhydrous diethyl ether. Upon completion of the addition, the mixture was kept at a temperature of −40° to −50° C. for one hour. Next and under identical conditions as to temperature 44.4 g. (0.17 mol) of 4-bromobenzophenone in 200 ml. of anhydrous tetrahydrofuran and 100 ml. of anhydrous diethyl ether were added drop-wise and the mixture was kept under the same conditions for another 3.5 hours. Cooling was stopped and the mixture was allowed to reach ambient temperature in ½ hour. It was then poured out into about 250 ml. of a sodium chloride solution. The aqueous layer was separated and discarded, the organic solvents layer was washed with 100 ml. of a sodium chloride solution, dried and concentrated. The residual oil was brought to crystallisation by addition of a very small amount of diethyl ether. Purification was brought about by crystallisation from warm ethanol to which some acetone was added. Melting point of the product was 138°–140° C.

B. Preparation of α-(p-bromophenyl)-α-phenylimidazole-2-methanol.

A mixture of 24.8 g. (0.052 mol) of α-(p-bromophenyl)-α-phenyl-1-(toluene-p-sulphonyl)imidazole-2-methanol, 160 ml. of 2 N hydrochloric acid solution (0.156 mol) and about 500 ml. of water was boiled under reflux for 5 hours. After cooling the mixture was made alkaline by addition of ammonia. The precipitated solid was collected, treated with activated carbon in boiling toluene and crystallised from toluene. Melting point of the product was 156°–158° C.

EXAMPLE II

A. Preparation of α,α-bis(p-fluorophenyl)-1-(toluene-p-sulphonyl)-imidazole-2-methanol.

Using the procedure described in Example IA, but substituting an equivalent amount of 4,4'-difluorobenzophenone (J. P. Picard et al., Can. J. Res. 28 B (1950) 56) for the 4-bromobenzophenone, an oil was obtained from which the above-mentioned compound crystallised upon addition of some cold diethyl ether. It was purified by boiling with petroleum ether (boiling range 40°–60° C.) and next with diethyl ether followed by crystallisation from ethanol. Its melting point was 149°–151° C.

B. Preparation of α,α-bis(p-fluorophenyl)imidazole-2-methanol.

A mixture of 10 g. (0.0227 mol) of α,α-bis(p-fluorophenyl)-1-(toluene-p-sulphonyl)imidazole-2-methanol, 34 ml. of 2 N hydrochloric acid solution (0.0681 mol) and 225 ml. of water was boiled under reflux for 5 hours. After cooling, the mixture was made alkaline by addition of ammonia. The base obtained was crystallised from isopropyl alcohol; its melting point was 198°–200° C.

EXAMPLE III

A. Preparation of α,α-bis(p-chlorophenyl)-1-(toluene-p-sulphonyl)-imidazole-2-methanol.

Using the procedure described in Example IA, but substituting an equivalent amount of 4,4'-dichlorobenzophenone for the 4-bromobenzophenone, a reaction mixture was obtained which was poured into a mixture of acetic acid and water. The organic solvents layer was separated, washed, dried and concentrated. The residual oil was brought to crystallisation by addition of some diethyl ether. The solid was separated and the filtrate concentrated and again subjected to the same treatment. This course of action was repeated till five batches of solid were obtained, of which the last three contain the desired product in impure form. They were mixed and boiled with petroleum ether (boiling range 40°–60° C.) repeatedly. Final purification was carried out by crystallisation from ethanol. Melting point of the product was 151°–153° C.

B. Preparation of α,α-bis(p-chlorophenyl)imidazole-2-methanol.

A mixture of 13 g. of α,α-bis(p-chlorophenyl)-1-(toluene-p-sulphonyl)imidazole-2-methanol, 6 ml. of concentrated hydrochloric acid solution, 6 ml. of water and 60 ml. of acetic acid was boiled under reflux for 1.5 hours. The desired compound was crystallised from warm toluene containing a small amount of isopropyl alcohol and thereafter from boiling diethyl ether to which some tetrahydrofuran had been added. Melting point of the product was 195°–197° C.

15 g. of the compound were dissolved in acetone and a solution of hydrogen chloride in ethanol was added. After addition of a small amount of petroleum ether (boiling range 60°–80° C.) a precipitate was obtained, consisting of the hydrochloride. The salt was washed with diethyl ether and crystallised from a mixture of ethanol and petroleum ether (boiling range 60°–80° C. Melting point above 200° C. with decomposition.

EXAMPLE IV
Preparation of α-(p-chlorophenyl)-α-phenylimidazole-2-methnaol.

To 5.6 g. of lithium in 150 ml. of anhydrous diethyl ether in a nitrogen atmosphere 44.5 g. of butyl bromide in 100 ml. of diethyl ether were added drop-wise at a temperature of −10° C. Upon completion of the reaction after 2 hours, the solution was filtered and added drop-wise to 55.5 g. of 1-(toluene-p-sulphonyl)imidazole dissolved in 450 ml. of anhydrous tetrahydrofuran and 225 ml. of anhydrous diethyl ether at a temperature of −30° C. After 1 hour, 58.6 g. of 4-chlorobenzophenone, dissolved in 300 ml. of anhydrous tetrahydrofuran and 150 ml. of anhydrous diethyl ether, were added drop-wise at −30° C. The mixture was kept at a temperature of −40° to −50° C. for 3 hours, allowed to return to ambient temperature and washed twice with water. The organic solvents layer was concentrated and 500 ml. of glacial acetic acid, 50 ml. of 36% hydrochloric acid solution and 50 ml. of water were added. The mixture was boiled under reflux for 1.5 hours. Glacial acetic acid was removed as completely as possible and water and diethyl ether were added.

The ether layer containing unreacted ketone and the aqueous oily layer containing the desired compound as the hydrochloride salt were separated. The aqueous layer was made alkaline by addition of 2 N sodium hydroxide solution and extracted with diethyl ether. The ether layer was acidified with 36% hydrochloric acid solution and extracted with water. The aqueous layer was treated with activated charcoal, made alkaline with 2 N sodium hydroxide solution and again extracted with diethyl ether. The diethyl ether layer was dried and concentrated and the solid obtained crystallised from isopropyl alcohol. Melting point of the product was 162°–165° C.

EXAMPLE V

Preparation of
α-(p-chlorophenyl)-α-phenylimidazole-2-methanol.

A solution of 17.2 g. of 2-benzoylimidazole (A. Sonn and P. Greif, Ber. 66 (1933), 1900) in 100 ml. of anhydrous tetrahydrofuran was added drop-wise to a Grignard reagent prepared from 5.8 g. of magnesium and 45.9 g. of 1-bromo-4-chlorobenzene in 150 ml. of anhydrous tetrahydrofuran. The reaction mixture was boiled under reflux for half an hour, cooled and poured onto a mixture of ice and hydrochloric acid. The solution was neutralized with concentrated ammonia solution and extracted with tetrahydrofuran. The organic solvents layer was dried and concentrated; the residue was crystallised from isopropyl alcohol. Melting point of the product was 162°–165° C.

EXAMPLE VI

A. Preparation of 1-[(benzyloxy)methyl]imidazole.

To 58 g. of imidazole-sodium in 200 ml. of anhydrous tetrahydrofuran 100 g. of benzyl chloromethyl ether were added drop-wise with stirring at a temperature of 0° to 5° C. Cooling was discontinued after one hour. The mixture was left standing overnight and thereafter concentrated. The residue was treated with 2 N hydrochloric acid solution and with diethyl ether. The acidic aqueous layer was made alkaline with potassium carbonate and extracted with chloroform. The chloroform layer was treated with activated carbon, dried and concentrated. The residue was subjected to distillation. Boiling point 147° C./3 mm.Hg.

B. Preparation of
1-[(benzyloxy)methyl]-α-(p-chlorophenyl)-α-phenylimidazole-2-methanol.

To a solution of 11.8 g. of 1-[(benzyloxy)methyl]imidazole in 100 ml. of anhydrous tetrahydrofuran and 50 ml. of anhydrous diethyl ether a solution of 38 ml. of a 20% butyllithium suspension in hexane dissolved in 75 ml. of anhydrous diethyl ether was added drop-wise with stirring at room temperature. Thereafter a solution of 14.6 g. of 4-chlorobenzophenone in 100 ml. of anhydrous tetrahydrofuran and 50 ml. of anhydrous diethyl ether was added drop-wise at room temperature. The mixture was kept for three hours and then extracted with a dilute acid solution. The acidic aqueous layer was made alkaline with 2 N sodium hydroxide solution and extracted with diethyl ether. Part of the ether was removed by evaporation and the residue washed with water. The ether solution was again concentrated and the desired compound crystallised from a mixture of toluene and petroleum ether (boiling range 28°–40° C.). Melting point of the product was 114.5°–117° C.

C. Preparation of
α-(p-chlorophenyl)-α-phenylimidazole-2-methanol.

About 17 g. (0.042 mol) of 1-[(benzyloxy)methyl]-α-(p-chlorophenyl)-α-phenylimidazole-2-methanol was boiled under reflux in a mixture of 85 ml. of glacial acetic acid, 8.5 ml. of water and 8.5 ml. of concentrated hydrochloric acid solution. Acetic acid was removed by evaporation and the base was liberated by addition of 2 N sodium hydroxide solution. It was crystallised from isopropyl alcohol. Melting point of the product was 162°–165° C.

EXAMPLE VII

A. Preparation of
α,α-bis(p-chlorophenyl)-1-(methoxymethyl)-imidazole-2-methanol.

To a solution of 11.2 g. (0.1 mol) of 1-(methoxymethyl)-imidazole and 13.9 g. (0.12 mol) of N,N,N',N'-tetramethylethylenediamine in 150 ml. of anhydrous tetrahydrofuran 51 ml. (0.12 mol) of n-butyllithium solution in hexane was added with stirring over a period of about one hour and at a temperature of −60° C. Stirring was continued for another 2 hours at −60° C. Cooling was discontinued and 25.1 g. (0.1 mol) of 4,4'-dichlorobenzophenone in 150 ml. of anhydrous tetrahydrofuran was added drop-wise. The mixture was stirred for 6 hours at room temperature and decomposed by addition of 15 ml. of water. Lithium hydroxide was removed by filtration and the filtrate was concentrated. A 2 N hydrochloric acid solution was added and the mixture was extracted with liberal amounts of diethyl ether. The acidic aqueous solution was made alkaline by addition of potassium carbonate and extracted with diethyl ether, toluene and ethyl acetate. The organic solvent solutions were combined, dried and concentrated. The solid was purified by crystallisation from toluene; its melting point was 145°–146° C.

B. Preparation of
α,α-bis(p-chlorophenyl)imidazole-2-methanol.

Using the procedure described in Example VIC but substituting an equivalent amount of α,α-bis(p-chlorophenyl)-1-(methoxymethyl)imidazole-2-methanol for the 1-[(benzyloxy)methyl]-α-(p-chlorophenyl)-α-phenylimidazole-2-methanol, α,α-bis(p-chlorophenyl)imidazole-2-methanol was obtained. Melting point of the product was 195°–197° C.

EXAMPLE VIII

A. Preparation of
α-(p-fluorophenyl)-1-(methoxymethyl)-α-phenylimidazole-2-methanol.

Using the procedure described in Example VIIA but substituting an equivalent amount of 4-fluorobenzophenone for the 4,4'-dichlorobenzophenone, α-(p-fluorophenyl)-1-(methoxymethyl)-α-phenylimidazole-2-methanol was obtained. Its melting point was 149.5°–150.5° C. after crystallisation from acetone.

B. Preparation of
α-(p-fluorophenyl)-α-phenylimidazole-2-methanol.

Using the procedure described in Example VIC but substituting an equivalent amount of α-(p-fluorophenyl)-1-(methoxymethyl)-α-phenylimidazole-2-methanol for the 1-[(benzyloxy)methyl]-α-(p-chlorophenyl)-α-phenylimidazole-2-methanol, α-(p-fluorophenyl)-α-phenylimidazole-2-methanol was obtained. Its melting point was 199–200.5° C. after crystallisation from acetone.

EXAMPLE IX

A. Preparation of
α,α-bis(p-bromophenyl)-1-(toluene-p-sulphonyl)-imidazole-2-methanol.

Using the procedure described in Example IA but substituting an equivalent amount of 4,4'-dibromobenzophenone, dissolved in a 6:1:1 mixture of anhydrous tetrahydrofuran:benzene:diethyl ether for the 4-bromobenzophenone, α,α-bis(p-bromophenyl)-1-(toluene-p-sulphonyl)imidazole-2-methanol was obtained. Its melting point was 144°-146° C. after crystallisation from isopropyl alcohol.

Some unreacted ketone may be recovered by addition of diethyl ether to the residue.

B. Preparation of α,α-bis(p-bromophenyl)imidazole-2-methanol.

Using the procedure described in Example IB but substituting an equivalent amount of α,α-bis(p-bromophenyl)-1-(toluene-p-sulphonyl)imidazole-2-methanol for the α-(p-bromophenyl)-α-phenyl-1-(toluene-p-sulphonyl)imidazole-2-methanol, α,α-bis(p-bromophenyl)imidazole-2-methanol was obtained. Its melting point was 192°-194° C. after crystallisation from isopropyl alcohol.

EXAMPLE X

A. Preparation of α-(o-chlorophenyl)-α-phenyl-1-(toluene-p-sulphonyl)-imidazole-2-methanol.

Using the procedure described in Example IA but substituting an equivalent amount of 2-chlorobenzophenone (J. Amer. Chem. Soc. 66, 534, (1944)) for the 4-bromobenzophenone, α-(o-chlorophenyl)-α-phenyl-1-(toluene-p-sulphonyl)imidazole-2-methanol was obtained. Its melting point was 165°-167° C. after crystallisation from toluene.

B. Preparation of α-(o-chlorophenyl)-α-phenylimidazole-2-methanol.

Using the procedure described in Example IB but substituting an equivalent amount of α-(o-chlorophenyl)-α-phenyl-1-(toluene-p-sulphonyl)imidazole-2-methanol for the α-(p-bromophenyl)-α-phenyl-1-(toluene-p-sulphonyl)imidazole-2-methanol, α-(o-chlorophenyl)-α-phenylimidazole-2-methanol was obtained. Its melting point was 186°-188° C. after crystallisation from isopropyl alcohol.

EXAMPLE XI

A. Preparation of α-(p-chlorophenyl)-α-phenyl-1-(toluene-p-sulphonyl)-imidazole-2-methanol.

Using the procedure described in Example IA but substituting an equivalent amount of 4-chlorobenzophenone for the 4-bromobenzophenone, α-(p-chlorophenyl)-α-phenyl-1-(toluene-p-sulphonyl)imidazole-2-methanol was obtained. Its melting point was 116°-118° C. after crystallisation from a mixture of diethyl ether and petrolleum ether (boiling range 28°-40° C.).

B. Preparation of α-(p-chlorophenyl)-α-phenylimidazole-2-methanol.

Using the procedure described in Example IB but substituting an equivalent amount of α-(p-chlorophenyl)-α-phenyl-1-(toluene-p-sulphonyl)imidazole-2-methanol for the α-(p-bromophenyl)-α-phenyl-1-(toluene-p-sulphonyl)imidazole-2-methanol, α-(p-chlorophenyl)-α-phenylimidazole-2-methanol was obtained. Its melting point was 163°-165° C.

EXAMPLE XII

Preparation of α-(m-chlorophenyl)-α-phenylimidazole-2-methanol as the hydrogen maleate.

Using the procedure described in Example V but substituting an equivalent amount of 1-bromo-3-chlorobenzene for the 1-bromo-4-chlorobenzene, α-(m-chlorophenyl)-α-phenylimidazole-2-methanol was obtained and purified by crystallisation from a mixture of toluene and petroleum ether (boiling range 28°-40° C.). Melting point 174°-175° C.

The compound was converted into the maleate by dissolving it in diethyl ether and adding a solution of maleic acid in the same solvent. The salt was crystallised twice from a mixture of isopropyl alcohol and diethyl ether and thereafter from a mixture of acetone and diethyl ether. Its melting point was 151°-153° C.

EXAMPLE XIII

Preparation of α,α-bis(p-chlorophenyl)-4,5-dimethyl-1-(1-propenyl)-imidazole-2-methanol.

In the course of one hour, 40 ml. (0.085 mol) of a 20% butyl lithium solution in n-hexane were added dropwise with stirring, under a nitrogen atmosphere at −60° C. to a solution of 10.4 g (0.0765 mol) of 1-allyl-4,5-dimethyl-imidazole and 9.3 g (0.080 mol) of N,N,N',N'-tetramethylethylenediamine in 125 ml. of anhydrous tetrahydrofuran. Stirring was continued for another two hours at −60° C. and then 19.5 g (0.078 mol) of 4,4'-dichlorobenzophenone in 100 ml of anhydrous tetrahydrofuran were added dropwise. The reaction mixture was kept standing overnight at room temperature and then 15 ml. of water and some pieces of solid carbon dioxide were added. The mixture was filtered and the filtrate was concentrated. The residue was extracted with a mixture of diethyl ether and 2 N hydrochloric acid. The aqueous phase was made alkaline with potassium carbonate and extracted with diethyl ether. The extract was dried over sodium sulphate and concentrated. The residue was extracted again with 2 N hydrochloric acid and diethyl ether and the aqueous phase was made alkaline again with potassium carbonate. The solid matter formed was filtered off and dissolved in boiling petroleum ether (boiling range 60°-80° C.). The undissolved material was filtered off and the petroleum ether was distilled off. The residue was taken up in a very small amount of diethyl ether. The solution was cooled in a mixture of carbon dioxide and acetone and the precipitate was filtered off. α,α-Bis(p-chlorophenyl)-4,5-dimethyl-1-(1-propenyl)imidazole-2-methanol was obtained. Melting point 127°-128° C.

EXAMPLE XIV

A. Preparation of α,α-bis(p-fluorophenyl)-1-(methoxymethyl)imidazole-2-methanol.

Using the procedure of Example VIIA but substituting an equivalent amount of 4,4'-difluorobenzophenone for the 4,4'-dichlorobenzophenone, α,α-bis(p-fluorophenyl)-1-(methoxymethyl)imidazole-2-methanol was obtained. Melting point 133° C.

B. Preparation of α,α-bis(p-fluorophenyl)imidazole-2-methanol.

Using the procedure described in Example VIC but substituting an equivalent amount of α,α-bis(p-fluorophenyl)-1-(methoxymethyl)imidazole-2-methanol for the 1-[(benzyloxy)-methyl]-α-(p-chlorophenyl)-α-phenylimidazole-2-methanol, α,α-bis(p-fluorophenyl)imidazole-2-methanol was obtained. Melting point 198°–200° C.

EXAMPLE XV

Preparation of α,α-bis(p-trifluoromethyl-phenyl)imidazole-2-methanol hydrochloride.

To a solution of 2.8 g. (0.025 mol) of 1-(methoxymethyl)-imidazole and 3.5 g. (0.03 mol) of N,N,N',N'-tetramethylethylenediamine in 50 ml. of anhydrous tetrahydrofuran a butyllithium solution, prepared from 0.5 g. (0.075 g. at) of lithium and 4.1 g. (0.030 mol) of butyl bromide in 40 ml. of anhydrous diethyl ether, was added drop-wise with stirring at a temperature of −60° C. and under a nitrogen atmosphere. After 2 hours, 8 g. (0.025 mol) of 4,4'-bis(trifluoromethyl)benzophenone in 60 ml. of anhydrous tetrahydrofuran were added at −60° C. The solution was kept standing overnight at room temperature and it was then decomposed with 50 ml. of water and extracted with diethyl ether. The extract was dried over sodium sulphate and the solvent was distilled off. The benzophenone starting material, present in the residue, was dissolved by boiling with petroleum ether (boiling range 40°–60° C.) and removed. The residue was then dissolved in a mixture of 75 ml. of acetic acid, 7.5 ml. of water and 75 ml. of concentrated hydrochloric acid, and the solution was refluxed for 5 hours. The liquid was distilled off and the residue was extracted with a mixture of 2 N hydrochloric acid and diethyl ether. The ethereal layer was dried over sodium sulphate. The sodium sulphate was washed with acetone. The solutions in ether and acetone were combined and the solvents were distilled off. The residue was washed with diethyl ether and filtered with suction. There was obtained α,α-bis(p-trifluoromethyl-phenyl)imidazole-2-methanol hydrochloride. Melting point 210°–216° C. (with decomposition).

EXAMPLE XVI

A. Preparation of 1-(methoxymethyl)-α-phenyl-α-(m-trifluoromethyl-phenyl)imidazole-2-methanol.

Under a nitrogen atmosphere and at a temperature between −60° and −65° C. a butyllithium solution, prepared from 2.04 g. (0.29 g. at) of lithium and 15.8 g. (0.116 mol) of butyl bromide in 130 ml. of anhydrous diethyl ether, was added drop-wise to a solution of 9.8 g. (0.088 mol) of 1-(methoxymethyl)imidazole and 10.2 g. (0.088 mol) of N,N,N',N'-tetramethylethylenediamine in 250 ml. of anhydrous tetrahydrofuran. After 2 hours stirring, a solution of 22 g. (0.088 mol) of 3-(trifluoromethyl)benzophenone in 150 ml. of anhydrous tetrahydrofuran were added dropwise to the reaction mixture at a temperature between −60° and −65° C. The reaction mixture was stirred for one hour at −65° C. and it was then kept standing overnight at room temperature. Then 20 ml. of water were added to the reaction mixture and the solvents were distilled off. The residue was dissolved in dilute hydrochloric acid and the solution was washed with diethyl ether and made alkaline with potassium carbonate. The solid substance formed was filtered off and dissolved in chloroform. The solution was dried over sodium sulphate, the solvent was distilled off and the residue was crystallised from isopropyl alcohol. 1-(Methoxymethyl)-α-phenyl-α-(m-trifluoromethyl-phenyl)imidazole-2-methanol was obtained. Melting point 152.5°–153.5° C.

B. Preparation of α-phenyl-α-(m-trifluoromethyl-phenyl)imidazole-2-methanol.

A mixture of 13 g. (0.037 mol) of 1-methoxymethyl-α-phenyl-α-(m-trifluoromethyl-phenyl)imidazole-2-methanol, 100 ml. of glacial acetic acid, 10 ml. of concentrated hydrochloric acid and 10 ml. of water was refluxed for three hours. After cooling, the liquid was distilled off and the residue was dissolved in a small amount of ethanol. The solution was made alkaline with 2 N sodium hydroxide solution and the alcohol was evaporated. The remaining aqueous phase was then extracted with diethyl ether. The extract was dried over sodium sulphate and the ether was distilled off. The residue was crystallised from toluene, the toluenic solution being decolorised with active charcoal. There was obtained α-phenyl-α-(m-trifluoromethyl-phenyl)imidazole-2-methanol. Melting point 151.5°–152.5° C.

EXAMPLE XVII

A. Preparation of 1-(methoxymethyl)-α-phenyl-α-(p-trifluoromethyl-phenyl)imidazole-2-methanol.

A butyllithium solution, prepared from 1.02 g. (0.145 g. at.) of lithium and 7.9 g. (0.058 mol) of butyl bromide in 70 ml. of anhydrous diethyl ether, was added dropwise at −60° C. to −65° C. under a nitrogen atmosphere to a solution of 4.9 g. (0.044 mol) of 1-(methoxymethyl)imidazole and 3.1 g. (0.044 mol) of N,N,N',N'-tetramethylethylenediamine in 125 ml. of anhydrous tetrahydrofuran. The reaction mixture was kept standing for 2 hours at −60° to −65° C. and then 11 g. (0.044 mol) of 4-(trifluoromethyl)benzophenone, dissolved in 75 ml. of anhydrous tetrahydrofuran, were added dropwise. The temperature was maintained at −65° C. for one hour and then the reaction mixture was allowed to attain room temperature overnight. 10 ml. of water and solid carbon dioxide were added and the solvent was distilled off. The residue was dissolved in dilute hydrochloric acid, the solution was washed with diethyl ether and made alkaline with potassium carbonate. The solid substance formed was filtered off and dissolved in chloroform. The solution was washed with water, dried over sodium sulphate and concentrated by evaporation of the solvent. The residue was crystallised from isopropyl alcohol. 1-(Methoxymethyl)-α-phenyl-α-(p-trifluoromethyl-phenyl)imidazole-2-methanol was obtained. Melting point 158°–159° C.

B. Preparation of α-phenyl-α-(p-trifluoromethylphenyl)imidazole-2-methanol.

A mixture of 9 g. (0.025 mol) of 1-(methoxymethyl)-α-phenyl-α-(p-trifluoromethyl-phenyl)imidazole-2-methanol, 70 ml. of glacial acetic acid, 7 ml. of concentrated hydrochloric acid and 7 ml. of water was refluxed for 3.5 hours. After cooling, the liquid was distilled off and 2 N sodium hydroxide solution and a small amount of ethanol were added to the residue. The alcohol was distilled off and the aqueous phase was extracted with diethyl ether. The ethereal solution was washed with water and dried over sodium sulphate and the solvent was distilled off. The residue was first crystallised from a mixture of toluene and petroleum ether (boiling range 40°–60° C.) and subsequently from isopropyl alcohol. α-Phenyl-α-(p-trifluoromethylphenyl)imidazole-2-methanol was obtained. Melting point 174°–175.5° C.

EXAMPLE XVIII

Preparation of α,α-bis(p-chlorophenyl)-1-methoxymethylimidazole-2-methanol.

To a solution of 22.4 g. (0.2 mol) of 1-(methoxymethyl)imidazole in 150 ml. of anhydrous tetrahydrofuran 92 ml. (0.2 mol) of butyllithium solution (20% in hexane) was added drop-wise with stirring under a nitrogen atmosphere at −60° C. The reaction mixture was stirred for 2 hours, after which anhydrous carbon dioxide gas was introduced. After being stirred for one hour, the mixture was poured onto solid carbon dioxide. The lithium salt of 1-(methoxymethyl)imidazole-2-carboxylic acid precipitated. The salt was filtered off and washed with diethyl ether.

To a suspension of 16.2 g. (0.1 mol) of the lithium salt and 35 g. (0.35 mol) of triethylamine in 150 ml. of anhydrous dichloromethane 48.8 g. (0.45 mol) of chlorotrimethylsilane was added drop-wise with stirring under a nitrogen atmosphere. The mixture was stirred for 20 hours, then 300 ml. of anhydrous toluene was added and stirring was continued for another hour. The lithium salts formed were filtered off and the filtrate was concentrated by evaporation of the solvents. The residue, containing the trimethylsilyl ester of 1-(methoxymethyl)imidazole-2-carboxylic acid, was dissolved in 100 ml. of anhydrous tetrahydrofuran and added dropwise to a refluxing solution of a Grignard compound prepared from 8.1 g. (0.3 g. at.) of magnesium and 57.5 g. (0.3 mol) of 4-bromo-1-chlorobenzene in 150 ml. of anhydrous tetrahydrofuran. The mixture was refluxed for one hour and then decomposed in an ammonium chloride solution. The precipitate was filtered off and the filtrate was extracted with diethyl ether. The ethereal phase was extracted with 2 N hydrochloric acid and the acid extract was made alkaline with ammonia and extracted with diethyl ether. The ethereal extract was dried over sodium sulphate and the solvent was distilled off. The residue was twice crystallised from isopropyl alcohol. α,α-Bis-(p-chlorophenyl)-1-(methoxymethyl)imidazole-2-methanol was obtained. Melting point 145°–146° C.

The compound was converted into α,α-bis(p-chlorophenyl)imidazole-2-methanol as described in Example VII B.

EXAMPLE XIX

A preparation of the ethyl ester of 1-(methoxymethyl)imidazole-2-carboxylic acid.

At a temperature of −10° C., 27.5 g. (0.25 mol) of ethyl chloroformate was added drop-wise to a solution of 28 g. (0.25 mol) of 1-(methoxymethyl)imidazole and 25 g. (0.25 mol) of triethylamine in 125 ml. of anhydrous chloroform. The mixture was stirred at 0° C. and then kept standing for two days at room temperature. The precipitated triethylamine hydrochloride was filtered off and washed with diethyl ether. The filtrate was concentrated by evaporating the solvents and the residue was dissolved in diethyl ether. The solution was dried over sodium sulphate, the ether was distilled off and the residue was distilled. The ethyl ester of 1-(methoxymethyl)imidazole-2-carboxylic acid was obtained. Boiling point 120°–124°/2 mm. Hg.

B. Preparation of α,α-bis(p-chlorophenyl)-1-(methoxymethyl)imidazole-2-methanol.

The product was dissolved in 50 ml. of anhydrous tetrahydrofuran and added drop-wise to a refluxing solution of a Grignard compound prepared from 4.05 g. (0.15 g. at.) of magnesium and 28.7 g. (0.15 mol) of 4-bromo-1-chlorobenzene in 80 ml. of anhydrous tetrahydrofuran. The mixture was refluxed for one hour and then decomposed in an ammonium chloride solution. The precipitate was filtered off and the filtrate was extracted with diethyl ether. The ethereal phase was extracted with 2 N hydrochloric acid and the acid extract was made alkaline with ammonia and extracted with diethyl ether. The ethereal extract was dried over sodium sulphate and the solvent was distilled off. The residue was twice crystallised from isopropyl alcohol. α,α-Bis(p-chlorophenyl)-1-(methoxymethyl)imidazole-2-methanol was obtained. Melting point 145°–146° C.

EXAMPLE XX

A. Preparation of 1-(methoxymethyl)-4,5-dimethylimidazole.

At a temperature of 60° C., 500 mg. of picrinic acid and 15.6 g. (0.39 mol) of sodium hydroxide were added to a solution of 31 g. (0.32 mol) of 4,5-dimethylimidazole (H, Bredereck and G. Theilig, Chem. Ber. 86, 88 (1953)) in 150 ml. of acetonitrile. Then 29 g. (0.36 mol) of chloromethoxymethane were added drop-wise, which made the temperature rise to 80° C. The reaction mixture was refluxed for 6 hours and filtered. The filtrate was concentrated by distilling off the solvent and the residue was distilled. 1-(Methoxymethyl)-4,5-dimethylimidazole was obtained. Boiling point 80°–100° C./1.0 mm. Hg. Melting point of the hydrogen oxalate 102°–103° C.

B. Preparation of α,α-bis(p-chlorophenyl)-1-(methoxymethyl)-4,5-dimethylimidazole-2-methanol.

At a temperature of −60° C. and under a nitrogen atmosphere, 114 ml. (0.24 mol) of butyllithium solution (20% in hexane) were added drop-wise with stirring to a solution of 28 g. (0.20 mol) of 1-(methoxymethyl)-4,5-dimethylimidazole and 28 g. (0.24 mol) of N,N,N',N'-tetramethylethylenediamine in 200 ml. of anhydrous tetrahydrofuran. After 2 hours stirring, 50 g. (0.20 mol) of 4,4'-dichlorobenzophenone in 250 ml of anhydrous tetrahydrofuran were added drop-wise at −60° C. After being kept standing overnight, the reaction mixture was extracted with water and the organic phase was concentrated by distilling off the solvents. The residue was treated with 2 N hydrochloric acid and diethyl ether, which resulted in the formation of an organic and aqueous layer with an oily intermediate layer. The aqueous and oily layers were made alkaline with ammonia and extracted with diethyl ether. The extract was dried over sodium sulphate and the solvent was distilled off. The oily residue was thrice recrystallised from isopropyl alcohol. α,α-Bis(p-chlorophenyl)-1-(methoxymethyl)-4,5-dimethylimidazole-2-methanol was obtained. Melting point 151° C.

EXAMPLE XXI

A. Preparation of α-(o-tert.-butylphenyl)-α-phenyl-1-vinylimidazole-2-methanol.

To a solution of 28.8 g. (0.25 mol) of N,N,N',N'-tetramethylethylenediamine and 17.6 g. (0.19 mol) of 1-vinylimidazole in 300 ml. of anhydrous tetrahydrofuran, 14 ml. (0.25 mol) of 20% butyllithium in n-hexane were added drop-wise with stirring at −60° C., and under a nitrogen atmosphere over the course of one hour. Stirring was continued for 2 hours under the same conditions, after which a solution of 48 g. (0.20 mol) of 2-tert.-butylbenzophenone in 300 ml. of anhydrous tetrahydrofuran was added drop-wise. The reaction mixture was stirred for 3.5 hours, after which the cooling means was removed and stirring was continued overnight under the nitrogen atmosphere. The lithium complex obtained was then decomposed with 15 ml. of water and a large excess of solid carbon dioxide. The precipitate was filtered off, the filtrate was dried over sodium sulphate and the solvent was distilled off. The solid residue was twice crystallised from ethyl acetate to which a small amount of ethanol had been added. α-(o-tert.-Butylphenyl)-α-phenyl-1-vinylimidazole-2-methanol was obtained. Melting point 152°–153° C.

B. Preparation of α-(o-tert.-butylphenyl)-α-phenyl-imidazole-2-methanol.

To a solution of 10.0 g. (0.03 mol) of α-(o-tert.-butylphenyl)-α-phenyl-1-vinylimidazole-2-methanol in 180 ml. of pyridine and 180 ml. of 0.5 N methanolic sodium hydroxide, 360 ml. of a 4% aqueous potassium permanganate solution were added drop-wise at 20° to 30° C. After the addition was completed, 4.8 g. of solid potassium permanganate were added (total permanganate 0.12 mol). The manganese dioxide was filtered off. The filtrate was treated with active charcoal, concentrated almost to complete dryness and poured into water. The solid substance was filtered off, dissolved in warm acetone, decolorised with active charcoal and precipitated by addition of water. The precipitate was recrystallised from a mixture of acetone and water. α-(o-tert.-Butylphenyl)-α-phenylimidazole-2-methanol was obtained. Melting point 185°–186° C.

EXAMPLE XXII

A. Preparation of α-(p-tert.-butylphenyl)-α-phenyl-1-vinylimidazole-2-methanol.

This compound was prepared by the procedure described in Example XXI A using the following materials:

28.8 g. (0.25 mol) of N,N,N',N'-tetramethylethylenediamine,
17.6 g. (0.19 mol) of 1-vinylimidazole,
114 ml. (0.25 mol) of 20% butyllithium in n-hexane,
48 g. (0.20 mol) of p-tert.-butylbenzophenone.

The product was twice crystallised from a mixture of ethyl acetate and petroleum ether (boiling range 28°–40° C.).

Melting point 145°–147° C.

B. Preparation of α-(p-tert.-butylphenyl)-α-phenyl-imidazole-2-methanol.

This compound was prepared by the procedure described in Example XXI B using 22.6 g. (0.068 mol) of α-(p-tert.-butylphenyl)-α-phenyl-1-vinylimidazole-2-methanol, 820 ml. of 4% aqueous potassium permanganate and 11 g. of solid potassium permanganate (total permanganate 0.214 mol). After the manganese dioxide had been filtered off, the excess of potassium permanganate in the filtrate was reduced to manganese dioxide by addition of sodium bisulphite. The precipitate was filtered off and the organic solvents were distilled off. The remainder of the filtrate was poured into water and the oil thus obtained was dissolved in diethyl ether. The solution was washed four times with water and dried over sodium sulphate and the solvent was distilled off. The resulting oil was taken up in as little acetone as possible and brought to crystallisation by adding petroleum ether (boiling range 28°–40° C.). Melting point 166°–166° C.

EXAMPLE XXIII

A. Preparation of α,α-bis(p-tert.-butylphenyl)-1-vinylimidazole-2-methanol.

This compound was prepared by the procedure indicated in Example XXII A, using the following materials: 10 g. (0.03 mol) of 4,4'-di-tert.-butylbenzophenone, 19.5 ml. (0.04 mol) of 20% butyllithium in n-hexane, 3 g. (0.03 mol) of 1-vinylimidazole and 4.9 g. (0.04 mol) of N,N,N', N'-tetramethylethylenediamine. The product was crystallised from ethyl acetate. Melting point 169°–170° C.

B. Preparation of α,α-bis(p-tert.-butylphenyl)imidazole-2-methanol.

This compound was prepared by the procedure indicated in Example XXII B using 8 g. (0.02 mol) of α,α-bis(p-tert.-butylphenyl)-1-vinylimidazole-2-methanol, 250 ml. of 4% potassium permanganate solution and 3.3 g. of solid potassium permanganate (total permanganate 0.08 mol). After removal of manganese dioxide and excess permanganate, the organic solvents were distilled off and the remaining liquid was poured into water. A precipitate was formed, which was filtered off and crystallised from a mixture of isopropyl alcohol and petroleum ether (boiling range 28°–40° C.). Melting point 215°–216° C.

EXAMPLE XXIV

Preparation of α,α-bis(p-fluorophenyl)-1-(methoxymethyl)-imidazole-2-methanol.

To a solution of 11.2 g. (0.1 mol) of 1-(methoxymethyl)imidazole and 13.9 g. (0.12 mol) of N,N,N',N'-tetramethylethylenediamine in 150 ml. of anhydrous tetrahydrofuran 51 ml. (0.12 mol) of a butyllithium solution (20% in n-hexane) was added drop-wise over the course of one hour at −60° C., and under a nitrogen atmosphere. After the addition was completed, stirring was continued for another two hours. The cooling means was then removed and 25.1 g. (0.1 mol) of 4,4'-difluorobenzophenone in 150 ml. of anhydrous tetrahydrofuran were added drop-wise. The reaction mixture was stirred for 6 hours at room temperature and it was then decomposed with 15 ml. of water. The precipitated lithium hydroxide was filtered off and the filtrate was concentrated by distilling off the solvents. 2N Hydrochloric acid was added to the residue, after which the mixture was extracted with diethyl ether. The aqueous phase was made alkaline with 2N sodium hydroxide solution. The precipitate formed was filtered off, washed with water and twice crystallised from a mixture of isopropyl alcohol and petroleum ether (boiling range 40°–60° C.). α,α-Bis(p-fluorophenyl)-1-(methoxymethyl)imidazole-2-methanol was obtained. Melting point 133° C.

EXAMPLE XXV

A. Preparation of 4,5-diisobutyl-1-(methoxymethyl)imidazole hydrogen oxalate.

At a temperature of 60° C., 500 mg. of picrinic acid and 22 g. (0.55 mol) of sodium hydroxide were added to a suspension of 83 g. (0.46 mol) of 4,5-diisobutylimidazole (H. Bredereck and G. Theilig, Chem. Ber. 86, 88 (1953)) in 600 ml. of acetonitrile. Then 41 g. (0.51 mol) of chloromethoxy-methane were added drop-wise with stirring, which made the temperature rise to 80° C. The reaction mixture was refluxed for 2 hours and it was then shaken with water and diethyl ether. The ethereal phase was dried over sodium sulphate and the solvent was distilled off. An ethereal solution of oxalic acid was added to the residue, the precipitate was filtered off and four times crystallised from isopropyl alcohol. Melting point 135°–137° C.

B. Preparation of α,α-bis(p-chlorophenyl)-4,5-diisobutylimidazole-2-methanol hydrogen maleate.

Under a nitrogen atmosphere and at −60° C., a butyllithium solution, prepared from 1.0 g. (0.15 g. at.) of lithium and 8.2 g. (0.06 mol) of butyl bromide in 50 ml. of anhydrous diethyl ether, was added drop-wise with stirring to a solution of 11.2 g. (0.05 mol) of 4,5-diisobutyl-1-(methoxymethyl)imidazole and 7.0 g. (0.06 mol) of N,N,N',N'-tetramethylethylenediamine in 100 ml. of anhydrous tetrahydrofuran. The mixture was stirred for 2 hours and then 12.5 g. (0.05 mol) of 4,4'-dichlorobenzophenone in 100 ml. of anhydrous tetrahydrofuran were added drop-wise. The reaction mixture was kept standing overnight and it was then poured onto ice and extracted with diethyl ether. The extract was dried over sodium sulphate and the solvent was distilled off. The residue was thrice crystallised from petroleum ether (boiling range 60°–80° C.).

A solution of 5.0 g. of the substance obtained in 100 ml. of glacial acetic acid, 10 ml. of concentrated hydrochloric acid and 100 ml. of water, was refluxed for 5 hours. The liquid constituents were distilled off and ethyl alcohol was added to the residue until a clear solution was obtained. The solution was made alkaline with ammonia and extracted with diethyl ether. The extract was dried over sodium sulphate and the solvent was distilled off. The residue was dissolved in diethyl ether and the solution was extracted with 2N hydrochloric acid. The extract was made alkaline with ammonia and extracted with diethyl ether. The ethereal solution was dried over sodium sulphate and the ether was distilled off. To the residue an ethereal solution of maleic acid was added. The precipitate was filtered off and thrice crystallised from isopropyl alcohol. α,α-Bis(p-chlorophenyl)-4,5-diisobutylimidazole-2-methanol hydrogen maleate was obtained. Melting point 188°–189° C.

EXAMPLE XXVI

Preparation of α-(o-tert.-butylphenyl)-1-(methoxymethyl)-α-phenylimidazole-2-methanol.

Under a nitrogen atmosphere and at −60° C., 38 ml. (0.08 mol) of a butyllithium solution (20% in n-hexane) were added drop-wise over the course of 45 minutes to a mixture of 9.6 g. (0.08 mol) of N,N,N',N'-tetramethylethylenediamine and 7 g. (0.06 mol) of 1-(methoxymethyl)imidazole in 100 ml. of anhydrous tetrahydrofuran. The mixture was stirred for another two hours under the same conditions and then 16 g (0.0675 mol) of o-tert.-butylbenzophenone in 100 ml. of anhydrous tetrahydrofuran were added dropwise. After the addition was completed, the mixture was stirred for 2 hours at −60° C., and one hour at room temperature. The mixture was decomposed with 5 ml. of water, the precipitate was filtered off and the filtrate was dried over sodium sulphate and concentrated. The solid residue was crystallised from isopropyl alcohol. α-(o-tert.-Butylphenyl)-1-(methoxymethyl)-α-phenylimidazole-2-methanol was obtained. Melting point 149°–150° C.

EXAMPLE XXVII

A. Preparation of 1-allyl-4(or 5)-(p-chlorophenyl)imidazole

A mixture of 53,6 g (0.3 mol) of 4(5)-(p-chlorophenyl)imidazole, 14.4 g (0.36 mol) of sodiumhydroxide, 100 mg of picric acid and 150 ml of acetonitrile was heated to 60° C. under stirring. Then 25.3 g (0.33 mol) of freshly distilled allyl chloride were added dropwise. The mixture was refluxed for 5 hours and filtered. The filtrate was concentrated and water and diethyl ether were added to the residue. The ethereal phase was washed with water, dried over sodium sulphate and concentrated. The residue was distilled. 1-Allyl-4(or 5)-(p-chlorophenyl)imidazole was obtained. Boiling point 157°–170° C./0.5–1.0 mm.

B. Preparation of α,α,4(or 5)-tris(p-chlorophenyl)-1-(1-propenyl)imidazole-2-methanol In the course of half an hour 89 ml. (0.145 mol) of 15% butyl lithium in n-hexane were added dropwise under a nitrogen atmosphere at −60° to −70° C. to a solution of 28.4 g (0.13 mol) of 1-allyl-4(or 5)-(p-chlorophenyl)imidazole and 16.8 g (0.145 mol) of N,N,N',N'-tetramethylethylenediamine in 150 ml. of anhydrous tetrahydrofuran. The mixture was stirred for another two hours under the same conditions. Then a solution of 32.6 g (0.13 mol) of 4,4'-dichlorobenzophenone in 100 ml. of anhydrous tetrahydrofuran was added dropwise and after completion of the addition, the mixture was stirred for another hour. The cooling means were removed and the mixture was kept standing overnight at room temperature under the nitrogen atmosphere. The reaction mixture was then decomposed by stirring half an hour with 20 ml. of water. The organic phase was separated off, washed with dilute hydrochloric acid until it was clearly acid, washed with water and dried over sodium sulphate. The solvent was distilled off under reduced pressure. The residue was dissolved in a small amount of diethyl ether with a little methanol. By addition of petroleum ether (boiling range 40°–60° C.) a solid was precipitated, which was filtered off and twice crystallised from isopropyl alcohol. α,α,4(or 5)-Tris(p-chlorophenyl)-1-(1-propenyl)-imidazole-2-methanol was obtained. Melting point 137°–139° C.

C. Preparation of α,α4(5)-tris(p-chlorophenyl)imidazole-2-methanol

At 0°–5° C., 425 ml. of a 4% aqueous potassium permanganate solution were added dropwise in the course of one hour to a solution of 16.7 g (0.0356 mol) of α,α-4(or 5)-tris(p-chlorophenyl)-1-(1-propenyl)imidazole-2-methanol in a mixture of 220 ml. of pyridine and 220 ml. of 0.5N ethanolic sodium hydroxide. Then 4.4 g of potassium permanganate were added in small portions to the reaction mixture. The reaction mixture was kept standing overnight at room temperature. The manganese dioxide formed was filtered off, the filtrate was decolorized with sodium metabisulphite and active charcoal and the solvent was distilled off under reduced pressure. The residue was suspended in water. The aqueous phase was extracted with diethyl ether, the extract was dried over sodium sulphate and concentrated. The residue was dissolved in as little as possible boiling isopropyl alcohol. Petroleum ether (boiling range 60°–80° C.) was added, which caused α,α,4(5)-tris(p-chlorophenyl)imidazole-2-methanol to precipitate. The product was crystallised from a mixture of isopropyl alcohol and petroleum ether (boiling range 60°–80° C.). Melting point 184°–185° C.

EXAMPLE XXVIII

A. Preparation of α,α-bis(2,4-dichlorophenyl)-1-(methoxymethyl)-imidazole-2-methanol To a solution of 7.6 g (0.0676 mol) of 1-(methoxymethyl)imidazole and 8.1 g (0.0676 mol) of N,N,N',N'-tetramethylethylenediamine in 150 ml of anhydrous tetrahydrofuran were added dropwise under a nitrogen atmosphere at −60° C., 43 ml. (0.070 mol) of n-butyl lithium solution (15% in n-hexane). The solution was stirred at −60° C. for one hour. Then 23 g (0.0676 mol) of 2,2',4,4'-tetrachlorobenzophenone (prepared as described by S. D. Wilson and Yuan Ying Cheng, J. Org. Chem. 5, 223–6 (1940)) in 150 ml. of anhydrous tetrahydrofuran were added dropwise. The solution was stirred another hour at −60° C. and one night at room temperature. The reaction mixture was decomposed with 100 ml. of water and extracted with diethyl ether. The organic phase was dried over sodium sulphate and concentrated and the residue was extracted with a mixture of 2N hydrochloric acid and diethyl ether on which a solid substance was formed, which was crystallised from a mixture of isopropyl alcohol and diethyl ether. The product appeared to be the hydrochloride of the desired compound, contaminated with the compound without methoxymethyl group. Ammonia and diethyl ether were added to liberate the free base. The ethereal phase was concentrated and the residue was four times crystallised from a mixture of isopropyl alcohol and petroleum ether (boiling range 60°–80° C.). α,α-Bis-(2,4-dichlorophenyl)-1-(methoxymethyl)imidazole-2-methanol was obtained. Melting point 145.5°–146° C.

B. Preparation of α,α-bis(2,4-dichlorophenyl)imidazole-2-methanol

A solution of 10 g (0.023 mol) of α,α-bis(2,4-dichlorophenyl)-1-(methoxymethyl)imidazole-2-methanol in 150 ml. of glacial acetic acid, 15 ml. of concentrated hydrochloric acid and 15 ml. of water was refluxed for two hours and then concentrated. The residue was dissolved in a small amount of a mixture of ethanol and 2N hydrochloric acid and the solution was extracted with diethyl ether. The extract was dried over sodium sulphate and the ether was distilled off. Diethyl ether and petroleum ether (boiling range 60°–80° C.) were added, the solid substance was filtered off and twice crystallised from isopropyl alcohol with a little ethanol. α,α-Bis(2,4-dichlorophenyl)imidazole-2-methanol was obtained. Melting point 193° C.

EXAMPLE XXIX

A. Preparation of α-(p-tert.-butylphenyl-α-(p-chlorophenyl)-1-(methoxymethyl)imidazole-2-methanol This compound was prepared by the procedure described in Example XXVII B, using the following materials:

11.2 g (0.1 mol) of 1-(methoxymethyl)imidazole,
13.35 g (0.115 mol) of N,N,N',N'-tetramethylethylenediamine in 250 ml. of anhydrous tetrahydrofuran,
70 ml. (0.115 mol) of 15% butyl lithium in n-hexane,
27.3 g (0.1 mol) of 4-tert.-butyl-4'-chlorobenzophenone (F. A. Vingiello and C. K. Bradsher, J. Am. Chem. Soc. 71, 3572 (1949)) in 150 ml. of anhydrous tetrahydrofuran.

After decomposition of the reaction mixture with 25 ml. of water, the organic phase was separated off, washed thrice with an aqueous sodium chloride solution and dried over sodium sulphate. The solvent was distilled off and the residue was suspended in a small amount of cold diethyl ether. The solid substance was filtered off and twice crystallised from acetone. α-(p-tert.-Butylphenyl)-α-(p-chlorophenyl)-1-(methoxymethyl)imidazole-2-methanol was obtained. Melting point 162°–163° C.

B. Preparation of α-(p-tert.-butylphenyl)-α-(p-chlorophenyl)imidazole-2-methanol A mixture of 13 g (0.034 mol) of α-(p-tert.-butylphenyl)-α-(p-chlorophenyl)-1-(methoxymethyl)imidazole-2-methanol, 150 ml. of glacial acetic acid, 15 ml. of concentrated hydrochloric acid and 15 ml. of water was refluxed for 3½ hours. The reaction mixture was treated with active charcoal and concentrated. The residue was dissolved in diethyl ether and the solution was washed with water. To the ethereal phase an ethereal solution of oxalic acid was added. The precipitate thus formed was crystallised from ethanol with a small amount of methanol. The base was liberated by addition of sodium hydroxyde and extraction with diethyl ether. The ether was distilled off and the residue was crystallised from isopropyl alcohol. As the product obtained contained crystal isopropyl alcohol, it was dissolved in diethyl ether. The ethereal phase was washed with water and dried over sodium sulphate and the ether was distilled off. α-(p-tert.-Butylphenyl)-α-(p-chlorophenyl)imidazole-2-methanol was obtained. Melting point 95°–110° C. The melting point was not sharp but the NMR and IR spectra, the titrations and the elementary analysis were in conformity with the desired structure. Thin layer chromatography revealed only one component.

EXAMPLE XXX

A. Preparation of α-(2,4-dichlorophenyl)-α-(p-fluorophenyl)-1-(methoxymethyl)imidazole-2-methanol At −60° C. and under a nitrogen atmosphere, 44 ml. (0.072 mol) of n-butyl lithium (15% solution in n-hexane) was added dropwise under stirring to a solution of 7.8 g (0.07 mol) of 1-(methoxymethyl)imidazole and 8.1 g (0.072 mol) of N,N,N',N'-tetramethylethylenediamine in 100 ml of anhydrous tetrahydrofuran. The mixture was stirred for one hour and then 18.9 g (0.070 mol) of 2,4-dichloro-4'-fluorobenzophenone in 100 ml of anhydrous tetrahydrofuran were added at −60° C. The solution was stirred for one hour at −60° C. and kept standing overnight at room temperature. Then 50 ml of water were added and the solid matter formed was filtered off. The filtrate was extracted with tetrahydrofuran and diethyl ether. The organic phase was dried over sodium sulphate and the solvents were distilled off. Diethyl ether was added to the semisolid residue and the solid matter was filtered off. This product was combined with the solid matter obtained after the addition of water. The substance was twice crystallised from acetone with a small amount of dimethylformamide. α-(2,4-Dichlorophenyl)-α-(p-fluorophenyl)-1-(methoxymethyl)imidazole-2-methanol was obtained. Melting point 179° C.

B. Preparation of α-(2,4-dichlorophenyl)-α-(p-fluorophenyl)imidazole-2-methanol A solution of 12 g (0.031 mol) of α-(2,4-dichlorophenyl)-α-(p-fluorophenyl)-1-(methoxymethyl)imidazole-2-methanol, 150 ml. of glacial acetic acid, 15 ml. of concentrated hydrochloric acid and 15 ml. of water was refluxed for 5 hours. The dark brown solution was concentrated and water was added to the residue. The mixture was then made alkaline by addition of ammonia and extracted with diethyl ether. The organic phase was separated off, decolorized with active charcoal, dried over sodium sulphate and the ether was distilled off. The solid residue was twice crystallised from acetone, rewashed with petroleum ether (boiling range 60°-80° C.) and once crystallised from isopropyl alcohol. α-(2,4-Dichlorophenyl)-α-(p-fluorophenyl)imidazole-2-methanol was obtained. Melting point 193.5°-194° C.

EXAMPLE XXXI

A. Preparation of α-(2,4-dichlorophenyl)-1-(methoxymethyl)-α-phenylimidazole-2-methanol This compound was prepared by the procedure described in Example XXVII B, using the following materials:

9.8 g (0.088 mol) of 1-(methoxymethyl)imidazole,
10.4 g (0.09 mol) of N,N,N',N'-tetramethylethylenediamine,
100 ml. of anhydrous tetrahydrofuran,
62 ml. (0.10 mol) of 15% butyl lithium in n-hexane,
22.6 g (0.09 mol) of 2,4-dichlorobenzophenone in 100 ml. of anhydrous tetrahydrofuran.

The reaction mixture was decomposed with 75 ml. of water. The solid matter formed was filtered off and the aqueous phase of the filtrate was discarded. The organic phase was concentrated. The residue appeared to be identical to the solid matter filtered off. The combined solid substances were crystallised from isopropyl alcohol. α-(2,4-Dichlorophenyl)-1-(methoxymethyl)-α-phenylimidazole-2-methanol was obtained. Melting point 161°-161.5° C.

B. Preparation of α-(2,4-dichlorophenyl)-α-phenylimidazole-2-methanol

A mixture of 11 g (0.033 mol) of α-(2,4-dichlorophenyl)-1-(methoxymethyl)-α-imidazole-2-methanol, 90 ml. of glacial acetic acid, 9 ml. of water and 9 ml of concentrated hydrochloric acid was refluxed for 3 hours. The acetic acid was distilled off and the residue was dissolved in a mixture of water and ethanol. The solution was made alkaline with 2N aqueous sodium hydroxide, the alcohol was distilled off and the aqueous solution was filtered. The filtrate was extracted with diethyl ether and the extract was dried over sodium sulphate and concentrated. The residue and the solid matter filtered off were combined and crystallised from acetone with a small amount of ethanol. α-(2,4-Dichlorophenyl)-α-phenylimidazole-2-methanol was obtained. Melting point 176°-177° C.

EXAMPLE XXXII

Preparation of 1-allyl-α-(p-chlorophenyl)-α-phenylimidazole-2-methanol

A mixture of 3.4 g (0.028 mol) of freshly distilled allyl bromide, 7 g (0.025 mol) of α-(p-chlorophenyl)-α-phenylimidazole-2-methanol (prepared according to Example IV), 1.2 g (0.030 mol) of sodium hydroxide, 0.050 g of picric acid and 50 ml. of acetonitrile was refluxed for 5 hours. The warm reaction mixture was filtered and water was added to the filtrate. The precipitate formed was filtered off, washed with water and petroleum ether (boiling range 40°-60° C.) and three times crystallised from isopropyl alcohol. 1-Allyl-α-(p-chlorophenyl)-α-phenylimidazole-2-methanol was obtained. Melting point 165°-165.5° C.

EXAMPLE XXXIII

Preparation of α,α-bis(p-chlorophenyl)-1-vinylimidazole-2-methanol

At a temperature of −60° to −70° C. and under a nitrogen atmosphere, 25 ml. (0.04 mol) of 15% butyl lithium in n-hexane were added to a solution of 3.2 g (0.034 mol) of 1-vinylimidazole and 4.6 g (0.04 mol) of N,N,N',N'-tetramethylethylenediamine in 75 ml. of anhydrous tetrahydrofuran. The mixture was stirred for 2 hours and then 8.5 g (0.034 mol) of 4,4'-dichlorobenzophenone, dissolved in 75 ml. of anhydrous tetrahydrofuran were added dropwise under the same conditions. The reaction mixture was stirred for 2 hours at −60° to −70° C. and kept standing overnight at room temperature under the nitrogen atmosphere. Then 25 ml. of water and a small amount of acetic acid were added to the reaction mixture and the liquid was distilled off. Water was added to the residue and the solid matter was filtered off. The product was crystallised from a mixture of isopropyl alcohol, dimethylformamide and petroleum ether (boiling range 60°-80° C.). α,α-Bis(p-chlorophenyl)-1-vinylimidazole-2-methanol was obtained. Melting point 173.5°-174° C.

EXAMPLE XXXIV

Preparation of
α-phenyl-α-(p-trifluoromethylphenyl)-1-vinylimidazole-2-methanol

This compound was prepared by the procedure described in Example XXXIII, using the following materials:

8.5 g (0.034 mol) of p-trilfuoromethylbenzophenone,
3.2 g (0.034 mol) of 1-vinylimidazole,
4.6 g (0.04 mol) of N,N,N',N'-tetramethylethylenediamine,
25 ml. (0.04 mol) of 15% butyl lithium in n-hexane.

The compound was crystallised from a mixture of acetone and petroleum ether (boiling range 60°-80° C.). Melting point 173.5°-174° C.

EXAMPLE XXXV

Preparation of
1-benzyl-α-phenyl-α(p-trifluoromethylphenyl)-imidazole-2-methanol A solution of 14.2 g (0.09 mol) of 1-benzylimidazole (A. M. Roe, J. Chem. Soc., 1963, 2195) in 60 ml. of tetrahydrofuran was added dropwise at −20° to −30° C. under a nitrogen atmosphere to 0.1 mol phenyl lithium (prepared from 1.52 g (0.22 gr. at.) of lithium and 15.7 g (0.19 mol) of bromobenzene) in 70 ml. of diethyl ether. The reaction mixture was stirred for one hour and then 22.5 g (0.09 mol) of 4-(trifluoromethyl)benzophenone in 35 ml. of tetrahydrofuran were added dropwise. The reaction mixture was stirred under the nitrogen atmosphere for two hours at −20° to −30° C. and for 15 hours at room temperature. The mixture was then poured into a mixture of ice and water. The aqueous phase was twice extracted with diethyl ether and the combined extracts were concentrated. The residue was taken up in diethyl ether and the undissolved solid matter (ketone starting material) was filtered off. The ether was distilled off and the residue was again taken up in a small amount of diethyl ether. The undissolved material, which now appeared to be the desired product, was filtered off. This procedure (evaporating the ether and taking up the residue in ether again) was repeated a few times and the solid materials filtered off were combined. The substance was crystallised from isopropyl alcohol with a small amount of water. 1-Benzyl-α-phenyl-α-(p-trifluoromethylphenyl)-imidazole-2-methanol was obtained.

Melting point 167°-169° C.

EXAMPLE XXXVI

Preparation of
1-benzyl-α,α-bis(p-chlorophenyl)imidazole-2-methanol

A solution of 17.4 g (0.11 mol) of N-benzylimidazole in 40 ml. of anhydrous tetrahydrofuran was added dropwise in the course of one hour, at −20° to −30° C. and under a nitrogen atmosphere, to a phenyl lithium solution, prepared from 1.67 g (0.24 gr. at.) of lithium and 18.8 g (0.12 mol) of bromobenzene in 80 ml. of anhydrous diethyl ether. The mixture was heated for about one hour until a brightly red, homogenous solution was obtained. Subsequently a solution of 25.1 g (0.1 mol) of 4,4'-dichlorobenzophenone in 60 ml. of anhydrous tetrahydrofuran was added in the course of one hour at a temperature between −25° and −15° C. The reaction mixture was stirred for 15 hours at room temperature, under the nitrogen atmosphere and it was then poured on 200 g of ice. The aqueous phase was saturated with sodium chloride and the organic phase was separated off and concentrated. The residue was dissolved in a small amount of acetone and the solution was acidified with 2 N hydrochloric acid. Then some toluene was added and the precipitate formed was filtered off. The product was thrice crystallised from a mixture of isopropyl alcohol and petroleum ether (boiling range 28°-40° C.). 1-Benzyl-α,α-bis(p-chlorophenyl)imidazole-2-methanol was obtained. Melting point 167°-168° C.

EXAMPLE XXXVII

Preparation of
1-benzyl-α,α-bis(p-fluorophenyl)imidazole-2-methanol

Following the procedure of Example XXXVI, but substituting an equivalent amount of 4,4'-difluorobenzophenone (J. P. Picard and C. W. Kearns, Can. J. Research, 28 B, 56 (1950)) for the 4,4'-dichlorobenzophenone, a reaction mixture was obtained, which was poured into a mixture of ice and sodium chloride. The organic phase was separated off, dried over sodium sulphate and the solvent was distilled off. Diethyl ether was added to the residue and the undissolved material—consisting of the desired compound—was filtered off. The product was crystallised from isopropyl alcohol. 1-Benzyl-α,α-bis(p-fluorophenyl)imidazole-2-methanol was obtained. Melting point 176°-177° C.

EXAMPLE XXXVIII

Preparation of
1-benzyl-α-(o-chlorophenyl)-α-phenylimidazole-2-methanol

The reaction procedure of Example XXXVI was repeated with o-chlorobenzophene instead of 4,4'-dichlorobenzophenone. The ketone was added at a temperature between 0° and 5° C. The mixture was stirred overnight at room temperature and then poured on 200 ml. of ice. The aqueous phase was saturated with sodium chloride and the organic phase was separated off. The solvents were distilled off and diethyl ether was added to the residue. The undissolved material was filtered off and thrice crystallised from a mixture of chloroform and petroleum ether. (boiling range 40°-60° C.). 1-Benzyl-α-(o-chlorophenyl)-α-phenylimidazole-2-methanol was obtained. Melting point 167.5°-168° C.

EXAMPLE XXXIX

Preparation of
1-benzyl-α-(p-chlorophenyl)-α-phenylimidazole-2-methanol

The reaction procedure of Example XXXVIII was repeated with p-chlorobenzophenone instead of o-chlorobenzophenone. The reaction mixture was poured on ice and the organic phase was separated off and concentrated. The residue was dissolved in a small amount of acetone and 2 N hydrochloric acid was added to the solution. The mixture was extracted with diethyl ether and the remaining aqueous phase was extracted with chloroform. The chloroform extract was concentrated and the residue was shaken with 2 N sodium hydroxide solution on which the desired compound crystallised. The product was filtered off and twice crystallised from a mixture of acetone and petroleum ether (boiling range 28°-40° C.) and twice from ethanol. 1-Benzyl-α-(p-chlorophenyl)-α-phenylimidazole-2-methanol was obtained. Melting point 174°–175° C.

EXAMPLE XL

Preparation of α-(p-chlorophenyl)-1-phenethyl-α-phenylimidazole-2-methanol

A solution of 20 ml. 20% butyl lithium in n-hexane (0.043 mol) in 30 ml. of diethyl ether was added dropwise under a nitrogen atmosphere to a solution of 5.5 g (0.032 mol) of 1-phenethylimidazole (J. Am. Chem. Soc., 71, 4000 (1949)) in 100 ml. of diethyl ether. After the addition was completed, the reaction mixture was stirred for another hour at room temperature. Then a solution of 7.8 g (0.036 mol) of 4-chlorobenzophenone in 75 ml. of anhydrous diethyl ether was added dropwise. The reaction mixture was stirred for 3 hours and it was then poured into 200 ml of ice-water. The ethereal layer was separated off, dried over sodium sulphate and the ether was distilled off. The residue was crystallised from a mixture of ethanol and petroleum ether (boiling range 40°–60° C.). α-(p-Chlorophenyl)-1-(phenethyl-α-phenylimidazole-2-methanol was obtained. Melting point 164°–165° C.

EXAMPLE XLI

Preparation of α-(p-chlorophenyl)-1-methyl-α-phenylimidazole-2-methanol

A solution of 25.5 g (0.08 mol) of 20% butyl lithium in n-hexane in 50 ml. of anhydrous diethyl ether was added at room temperature to a solution of 5 g (0.06 mol) of 1-methylimidazole in 50 ml. of anhydrous diethyl ether. The reaction mixture was stirred for one hour and then a solution of 15.6 g (0.07 mol) of 4-chlorobenzophenone in diethyl ether was added dropwise. The reaction mixture was stirred for 3 hours and it was then poured into a mixture of ice and water. The solid matter was filtered off and crystallised from ethanol. α-(p-Chlorophenyl)-1-methyl-α-phenylimidazole-2-methanol was obtained. Melting point 185°–186° C.

EXAMPLE XLII

A. Preparation of 1-(p-chlorobenzyl)imidazole oxalate (1:1)

A mixture of 13.6 g (0.2 mol) of imidazole, 9.6 g (0.24 mol) of sodium hydroxide and 150 ml. of acetonitrile was stirred for one hour. Then 0.5 g of 50% picric acid in water and a few crystals of potassium iodide were added to the suspension. The homogenous reaction mixture obtained was heated to 50° C. and at this temperature a solution of 35.4 g (0.22 mol) of p-chlorobenzylchloride in 50 ml. of acetonitrile was added dropwise. The reaction mixture was then refluxed for 4 hours. After cooling, the solid matter (sodium chloride) was filtered off. The solvent was evaporated and the residue was distilled. The boiling range of the main fraction was 144°–166° C./0.6 mm. This product was dissolved in anhydrous diethyl ether and an ethereal solution of oxalic acid was added, which caused the desired oxalate to precipitate. The salt was crystallised from ethanol. Melting point 137.5°–139.5° C.

B. Preparation of 1-(p-chlorobenzyl)-α,α-bis(p-chlorophenyl)imidazole-2-methanol In the course of one hour, 64 ml. (0.105 mol) of 15% butyl lithium in n-hexane were added dropwise at −65° to −70° C. and under a nitrogen atmosphere, to a solution of 19.3 g (0.1 mol) of 1-(p-chlorobenzyl)imidazole (prepared from the oxalate described under (A) and 12.2 g (0.105 mol) of N,N,N',N'-tetramethylethylenediamine in 150 ml. of anhydrous tetrahydrofuran. The reaction mixture was stirred for one hour and then a suspension of 25.1 g (0.1 mol) of 4,4'-dichlorobenzophenone in 150 ml. of anhydrous tetrahydrofuran was added quickly under the same reaction conditions. Stirring was continued for one hour and then the cooling means was removed and the reaction mixture was kept standing overnight at room temperature. 20 ml. of water were added and the organic phase was separated off and concentrated. The residue was suspended in a mixture of water and diethyl ether. The solid matter formed was filtered off and the ethereal layer was separated off, dried over sodium sulphate and concentrated. The residue was twice crystallised from methanol. 1-(p-Chlorobenzyl)-α,α-bis-(p-chlorophenyl)imidazole-2-methanol was obtained. Melting point 171°–173° C.

EXAMPLE XLIII

Preparation of α,α-bis(p-chlorophenyl)-1-methylimidazole-2-methanol

To a suspension of 9.6 g (0.030 mol) of α,α-bis(p-chlorophenyl)imidazole-2-methanol (prepared according to Example III) in 100 ml. of acetonitrile, 500 mg of picric acid, 300 mg of potassium iodide and 1.45 g (0.036 mol) of sodium hydroxide were added at 60° C. The reaction mixture was stirred for one hour and then 4.7 g (0.033 mol) of methyl iodide in 25 ml. of acetonitrile were added dropwise at 55° C. The mixture was refluxed for four hours, the solvent was distilled off and the residue was extracted with a mixture of water and diethyl ether. The solid matter was filtered off and the ethereal phase was dried over sodium sulphate and concentrated. Diethyl ether was added to the residue and the solid matter was filtered off. The two portions of solid material were combined and twice crystallised from isopropyl alcohol and twice from toluene and rewashed with petroleum ether (boiling range 60°–80° C.). α,α-Bis(p-chlorophenyl)-1-methylimidazole-2-methanol was obtained. Melting point 190°–191° C.

EXAMPLE XLIV

Preparation of 1-(methoxymethyl)-α,α-bis(p-trifluoromethylphenyl)imidazole-2-methanol 9.1 Ml. (0.015 mol) of n-butyl lithium solution (15% in n-hexane) were added dropwise with stirring at −60° C. and under a nitrogen atmosphere to a solution of 1.7 g (0.015 mol) of 1-(methoxymethyl)imidazole and 1.8 g (0.015 mol) of N,N,N',N'-tetramethylethylenediamine in 75 ml. of anhydrous tetrahydrofuran. Stirring was continued for 1.5 hours and then 2.9 g (0.0091 mol) of 4,4'-bis(trifluoromethyl)benzophenone in 50 ml. of anhydrous tetrahydrofuran were added dropwise under the same conditions, which made the colour change from light red into very dark brown. The reaction mixture was kept standing overnight at room temperature and it was then decomposed by addition of 40 ml. of water. The mixture was extracted with diethyl ether and the extract was concentrated. The residue was extracted with a mixture of 2 N hydrochloric acid and diethyl ether. The ethereal phase was dried over sodium sulphate and the ether was distilled off. The residue was boiled a few times with petroleum ether (boiling range 40°–60° C.) to remove ketone starting material and it was then once crystallised from a mixture of toluene and petroleum ether (boiling range 28°–40° C.) twice from petroleum ether (boiling range 100°–140° C.). 1-(Methoxymethyl)-α,α-bis(p-trifluoromethylphenyl)imidazole-2-methanol was obtained. Melting point 160°–161° C.

EXAMPLE XLV

Preparation of 1-[(benzyloxy)methyl]-α,α-bis(p-chlorophenyl)imidazole-2-methanol A mixture of 125 ml. of acetonitrile, 9.2 g of α,α-bis(p-chlorophenyl)imidazole-2-methanol (prepared according to Example III) and 1.5 g of sodium hydroxide was stirred for one hour. To the—now homogeneous—reaction mixture 500 mg of picric acid and a few crystals of potassium iodide were added and the mixture was heated to 50° C. A solution of 5.2 g of benzyloxymethyl chloride in 50 ml. of acetonitrile was then added dropwise and the reaction mixture was subsequently refluxed for 4 hours. The mixture was cooled and filtered and the filtrate was concentrated under reduced pressure. The residue was suspended in water and the suspension was extracted with diethyl ether. The extract was dried over sodium sulphate and the ether was distilled off. The solid residue obtained was crystallized from isopropyl alcohol. The product was then boiled four times with 75 ml. of petroleum ether (boiling range 60°–80° C.), the petroleum ether being decanted each time, after which it was once again crystallized from isopropyl alcohol. The substance was dried in vacuo for 10 hours at 110° C. 1-[(Benzyloxy)methyl]-α,α-bis(p-chlorophenyl)imidazole-2-methanol was obtained. Melting point 139°–141° C.

EXAMPLE XLVI

Preparation of α,α-bis(p-chlorophenyl)-1-vinylimidazole-2-methanol 2.19 g (0.09 gr.at.) of magnesium and 10.9 g (0.1 mol) of ethyl bromide were converted into a Grignard compound in 50 ml. of refluxing anhydrous tetrahydrofuran. In the course of 5 minutes a solution of 8.46 g (0.09 mol) of 1-vinylimidazole in 20 ml. of anhydrous tetrahydrofuran was added with stirring to the refluxing mixture, after which the reaction mixture was refluxed for another two hours. A suspension of 22.6 g (0.09 mol) of 4,4'-dichlorobenzophenone in 50 ml. of anhydrous tetrahydrofuran was then added and refluxing was continued for 24 hours. The whole procedure was carried out under a nitrogen atmosphere. After cooling, the reaction mixture was poured into a mixture of ice, water and ammonium chloride. The mixture was then extracted with diethyl ether and the extract was washed with water, dried over sodium sulphate and concentrated. The solid residue was twice crystallized from a mixture of isopropyl alcohol and dimethyl formamide. α,α-Bis(p-chlorophenyl)-1-vinylimidazole-2-methanol was obtained. Melting point 173.5°–174° C.

EXAMPLE XLVII

Preparation of 1-benzyl-α,α-bis(p-chlorophenyl)imidazole-2-methanol

A solution of 19.2 g of α,α-bis(p-chlorophenyl)imidazole-2-methanol (prepared according to Example III B) and 3 g of sodium hydroxyde in 250 ml. of acetonitrile was refluxed for one hour with stirring. Then 500 mg of picric acid, a few crystals of potassium iodide and a solution of 11.3 g of benzyl bromide in 100 ml. of acetonitrile were added. Refluxing was then continued for 4 hours with stirring. The reaction mixture was kept standing overnight. The precipitate formed was filtered off and dissolved in 3 liter of diethyl ether. This solution was washed with a saturated sodium chloride solution, decolorized with active charcoal, dried over sodium sulphate and concentrated. The residue was crystallised from a mixture of methanol and diethyl ether. 1-Benzyl-α,α-bis(p-chlorophenyl)imidazole-2-methanol was obtained. Melting point 167°–168° C.

The invention includes within its scope pharmaceutical compositions containing, as the active ingredient, at least one of the therapeutically active compounds of general formula I, or non-toxic acid addition salt thereof, in association with a pharmaceutically acceptable carrier. The compositions may take any of the forms customarily employed for administration of therapeutic substances. Tablets and pills may be formulated in the usual manner with one or more pharmaceutically acceptable diluents or excipients, for example lactose or starch, and include materials of a lubricating nature, for example calcium or magnesium stearate. Capsules made of absorbable material, such as gelatin, may contain the active substance alone or in admixture with a solid or liquid diluent. The active substance, or an acid addition salt thereof, may also be made up in a form suitable for parenteral administration, i.e. as a suspension or emulsion in sterile water or an organic liquid usually employed for injectable preparations, for example a vegetable oil such as olive oil, or a sterile solution in water or an organic solvent.

The following Example illustrates the preparation of a pharmaceutical composition.

EXAMPLE XLVIII 50 g of α,α-bis(p-chlorophenyl)imidazole-2-methanol, sieved through a 40 mesh sieve (size of meshes 0.345 mm), 50 g of Avicel PH 101 (mycrocrystalline cellulose) are mixed together and gelatin capsules are filled each with 101 mg of the mixture so that each capsule contains 50 mg of active substance.

We claim:

1. An α,α-diarylimidazole-2-methanol of the formula

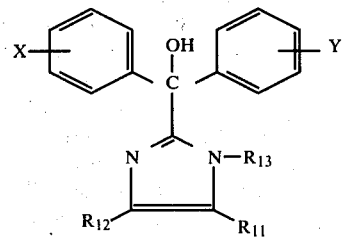

wherein X represents tert.butyl, trifluoromethyl, halogen or dihalogen, Y represents hydrogen, tert.butyl, trifluoromethyl, halogen or dihalogen, $R_{11}$ and $R_{12}$ are the same or different and each represents hydrogen, lower alkyl, phenyl or monohalogen-substituted phenyl and $R_{13}$ represents a hydrogen atom or—when $R_{11}$ and $R_{12}$ are hydrogen or one or both of them is lower alkyl—lower alkoxymethyl or phenyl(lower)alkoxymethyl or a non-toxic acid addition salt thereof.

2. A compound according to claim 1 in which X is 4-halogen, 4-trifluoromethyl or 4-tert.butyl, Y is hydrogen, 4-halogen, 4-trifluoromethyl or 4-tert.butyl and $R_{11}$ and $R_{12}$ are hydrogen, or a non-toxic acid addition salt thereof.

3. A compound according to claim 2 in which both X and Y are 4-chloro or X is 4-trifluoromethyl and Y is hydrogen.

4. α,α-Bis(p-chlorophenyl)imidazole-2-methanol or a non-toxic acid addition salt thereof according to claim 1.

5. α,α-Bis(p-chlorophenyl)-1-methoxymethyl-imidazole-2-methanol or a non-toxic acid addition salt thereof according to claim 1.

6. α-Phenyl-α-(p-trifluoromethylphenyl)imidazole-2-methanol or a non-toxic acid addition salt thereof according to claim 1.

7. 1-(Methoxymethyl)-α-phenyl-α-(p-trifluoromethylphenyl)imidazole-2-methanol or a non-toxic acid addition salt thereof according to claim 1.

8. A composition useful as an analgesic containing an analgesically effective amount of at least one compound defined in claim 1 in association with a pharmaceutically acceptable carrier.

* * * * *